United States Patent
Avagliano et al.

(10) Patent No.: US 10,486,130 B2
(45) Date of Patent: Nov. 26, 2019

(54) UREA SYNTHESIS REACTOR AND PROCESS

(71) Applicant: SAIPEM S.p.A., San Donato Milanese (IT)

(72) Inventors: Ugo Avagliano, San Donato Milanese (IT); Stefano Cicchinelli, San Donato Milanese (IT); Lino Carlessi, Dalmine (IT)

(73) Assignee: SAIPEM S.P.A., San Donato Milanese (IT)

(*) Notice: Subject to any disclaimer, the term of this patent is extended or adjusted under 35 U.S.C. 154(b) by 0 days.

(21) Appl. No.: 15/562,794

(22) PCT Filed: Apr. 1, 2016

(86) PCT No.: PCT/IB2016/051885
§ 371 (c)(1),
(2) Date: Sep. 28, 2017

(87) PCT Pub. No.: WO2016/157154
PCT Pub. Date: Oct. 6, 2016

(65) Prior Publication Data
US 2018/0280921 A1 Oct. 4, 2018

(30) Foreign Application Priority Data
Apr. 3, 2015 (IT) .............................. MI2015A0485

(51) Int. Cl.
*B01J 19/24* (2006.01)
*B01J 19/26* (2006.01)
(Continued)

(52) U.S. Cl.
CPC ............... *B01J 19/24* (2013.01); *B01J 4/004* (2013.01); *B01J 10/00* (2013.01); *B01J 19/26* (2013.01);
(Continued)

(58) Field of Classification Search
None
See application file for complete search history.

(56) References Cited

U.S. PATENT DOCUMENTS

| | | | |
|---|---|---|---|
| 3,446,601 A | 5/1969 | Heunks et al. | |
| 5,750,080 A * | 5/1998 | Pagani | B01D 3/22 422/607 |
| 2012/0068111 A1 | 3/2012 | Shaikh | |

FOREIGN PATENT DOCUMENTS

| | | |
|---|---|---|
| CN | 1224635 | 8/1999 |
| CN | 2616278 | 5/2004 |

(Continued)

OTHER PUBLICATIONS

Notification Concerning Submission, Obtention or Transmittal of Priority Document for International Application No. PCT/IB2016/051885 dated Jul. 1, 2016.
(Continued)

*Primary Examiner* — Amy C Bonaparte
(74) *Attorney, Agent, or Firm* — Neal, Gerber & Eisenberg LLP

(57) ABSTRACT

A urea synthesis reactor is provided that comprises a casing extending along an axis and a first and a second inlet tube inserted through respective through openings of the casing and respectively connected, inside the casing, to a light phase distributor and to a heavy phase distributor configured to feed the reactor with a light phase containing carbon dioxide and a heavy phase containing ammonia, respectively; the light phase distributor comprises one or more tubular elements extending and/or distributed over the cross-section of the reactor and about the axis and provided with intake holes spaced apart from one another, so as to distribute said light phase in a plurality of intake points distributed transversely in the reactor and about the axis.

7 Claims, 7 Drawing Sheets

(51) Int. Cl.
　　　*B01J 10/00*　　　(2006.01)
　　　*B01J 4/00*　　　(2006.01)
　　　*C07C 273/04*　　　(2006.01)
(52) U.S. Cl.
　　　CPC ... *C07C 273/04* (2013.01); *B01J 2219/00006* (2013.01); *B01J 2219/185* (2013.01); *B01J 2219/1943* (2013.01); *Y02P 20/142* (2015.11)

(56) References Cited

FOREIGN PATENT DOCUMENTS

| DE | 102010053289 | 6/2012 |
|---|---|---|
| EP | 2 596 859 | 5/2013 |
| SU | 1648544 | 5/1991 |

OTHER PUBLICATIONS

International Search Report and Written Opinion for International Application No. PCT/IB2016/051885 dated Jul. 20, 2016.
PCT Demand for International Preliminary Examination and Reply to International Search Report and the associated Written Opinion for International Application No. PCT/IB2016/051885 dated Jan. 9, 2017.
Notification of Receipt of Demand by Competent International Preliminary Examining Authority (Form PCT/IPEA/402) for International Application No. PCT/IB2016/051885 dated Jan. 17, 2017.
Notification of Transmittal of the International Preliminary Report on Patentability (Form PCT/IPEA/416) for International Application No. International Application No. PCT/IB2016/051885 dated Mar. 2, 2017.

\* cited by examiner

PRIOR ART

UREA SYNTHESIS REACTOR AND PROCESS

PRIORITY CLAIM

This application is a national stage application of PCT/IB2016/051885, filed on Apr. 1, 2016, which claims the benefit of and priority to Italian Patent Application No. MI2015A000485, filed on Apr. 3, 2015, the entire contents of which are each incorporated by reference herein.

TECHNICAL FIELD

The present disclosure relates to a urea synthesis reactor and process.

BACKGROUND

As is known, urea is normally produced on an industrial scale via a direct biphasic reaction of ammonia and carbon dioxide under relatively high temperature and relatively high pressure conditions.

A typical urea synthesis reactor of a urea plant is fed with an essentially gaseous stream of carbon dioxide and an essentially liquid stream of ammonia/ammonium carbamate. The reagents are fed into the reactor from below, through a bottom part of the reactor and via respective distributors.

FIG. 1 schematically shows, in a simplified manner, the lower part of a typical urea synthesis reactor 1 of one known type.

In general, the reactor 1 extends along a vertical axis A and comprises a casing 2 internally defining a reaction chamber 3; the casing 2 has a basically cylindrical main portion 4 and a dome-shaped bottom portion 5 (in particular, substantially hemispherical). The bottom portion 5 is joined to the main portion 4 along an essentially circular peripheral edge 9, which lies on a plane substantially orthogonal to axis A.

The casing 2 is supported by a support frame 10, mechanically connected, in particular, to the bottom portion 5.

The reagents (carbon dioxide and ammonia/ammonium carbamate) are fed into the reactor 1 through respective dedicated distributors 15 and 16.

The distributors 15 and 16 are constituted by respective substantially vertical tubular elements, arranged to pass through the wall of the reactor 1, and precisely of the bottom portion 5, in respective openings made in said wall.

The tubular elements constituting the distributors 15 and 16 project upwards from the wall of the bottom portion 5 and form the so-called drilled pipes: each tubular element has a closed free end (located inside the reactor 1) and a plurality of lateral through holes, made in the lateral wall of the tubular element for a certain longitudinal length close to the free end.

The distributors 15 and 16 are placed in an eccentric position, for example diametrically opposed with respect to the central axis A of the reactor 1 and, in any case, generally on opposite sides of a vertical center-plane passing through the axis A of the reactor 1.

The distributors 15 and 16 constitute the end parts of respective inlet tubes bent in an elbow-shape: outside of the reactor, each tube comprises an elbow-shaped bend that connects the vertical tubular element with a horizontal section that passes through the frame 10.

A reactor with a reagent feed system such as this known type has certain drawbacks.

Apart from the related constructional complexity, mainly due to the use of elbow-shaped inlet tubes (which must normally be forged) and the need to perforate a bottom portion of the reactor, the largest drawback consists in that the vertical arrangement of the distributors does not allow uniform distribution of the reagents over the entire cross-section of the reactor.

In particular, the carbon dioxide, which due to its density constitutes the light phase in the urea synthesis reaction, tends to form a vertical column above the related distributor, in this way strongly limiting reaction kinetics, which would instead be favoured by the uniform distribution of carbon dioxide in small bubbles over the entire cross-section of the reactor. Even the distribution of the (liquid) heavy phase, formed of ammonia and ammonium carbamate, is not entirely satisfactory.

This unsatisfactory distribution of reagents, in particular of carbon dioxide, causes part of the volume of the reactor to remain unused (due to poor contact between the two phases), especially in the reactor's reagent inlet zone; this volume could instead be very productive as the concentration of the reagents is at its maximum here.

SUMMARY

One advantage of the present disclosure is to provide a urea synthesis reactor and process that enables overcoming certain of the drawbacks pointed out above of the known art; in particular, one advantage of the disclosure is that of improving the efficiency of known urea synthesis reactors and processes.

The present disclosure thus relates to a urea synthesis reactor comprising: a casing extending along an axis and having a main portion closed at opposite axial ends by two end caps. The urea synthesis reactor also comprises a first inlet tube inserted through a first opening of the casing and connected, inside the casing, to a light phase distributor including at least one tubular element extending, about the axis, into a cross-section of the casing. The at least one tubular element defines a plurality of spaced apart intake holes, wherein the light phase distributor is configured to distribute a light phase containing carbon dioxide to a plurality of intake points distributed transversely in the casing about the axis. The first opening is formed through a side wall of the main portion of the casing above a peripheral edge joining the main portion with a dome-shaped bottom portion of the casing. The urea synthesis reactor further comprises a second inlet tube inserted through a second opening of the casing and connected, inside the casing, to a heavy phase distributor configured to distribute a heavy phase containing ammonia. The second opening is formed through the side wall of the main portion of the casing above the peripheral edge joining the main portion with the dome-shaped bottom portion of the casing. The heavy phase distributor includes a substantially L-shaped tubular body having a substantially vertical tube portion defining a plurality of lateral through holes, wherein the tube portion extends downwards towards the dome-shaped bottom portion of the casing.

The present disclosure further relates to a urea synthesis process comprising supplying a light phase containing carbon dioxide and a heavy phase containing ammonia into a reactor extending along an axis and defining a reaction chamber wherein the light phase is supplied into the reactor through a first opening formed through a side wall of a main portion of a casing of the reactor. The first opening is above a peripheral edge joining the main portion of the casing with a dome-shaped bottom portion of the casing and the heavy phase is supplied into the reactor through a second opening formed through the side wall of the main portion of the casing of the reactor. The second opening is above the peripheral edge joining the main portion of the casing with the dome-shaped bottom portion of the casing. The urea synthesis processor further comprises distributing, at a plurality of intake points distributed transversely in the reactor about the axis, the light phase substantially uniformly in a cross-section of the reactor about the axis, and centrally directing the heavy phase downwards along the axis to radially distribute the heavy phase in the reaction chamber.

With respect to traditional configurations, the disclosure enables obtaining better and more rapid mixing of the light phase (carbon dioxide) with the heavy phase (ammonia/ammonium carbamate).

In particular, the disclosure achieves relatively better distribution of the carbon dioxide over the cross-section of the reactor, with consequent advantages in overall efficiency of the urea synthesis process.

Furthermore, carbon dioxide bubbles of relatively smaller diameter are formed, which are also propitious from the reaction efficiency viewpoint.

Additional features and advantages are described in, and will be apparent from the following Detailed Description and the figures.

BRIEF DESCRIPTION OF THE DRAWINGS

Further characteristics and advantages of the present disclosure will become clear from the description of the following non-limitative embodiments, with reference to the figures in the accompanying drawings, in which.

DETAILED DESCRIPTION

Referring now to the example embodiments of the present disclosure illustrated in FIGS. 2 to 9, FIG. 2 shows, in simplified and schematic form, the lower part of a urea synthesis reactor 1, specifically destined to perform the biphasic reaction for the direct synthesis of urea, at relatively high temperature and relatively high pressure, starting from carbon dioxide and ammonia with the intermediate formation of ammonium carbamate.

In general, the reactor 1 extends along a vertical axis A and comprises a casing 2 internally defining a reaction chamber 3.

Figure 1:
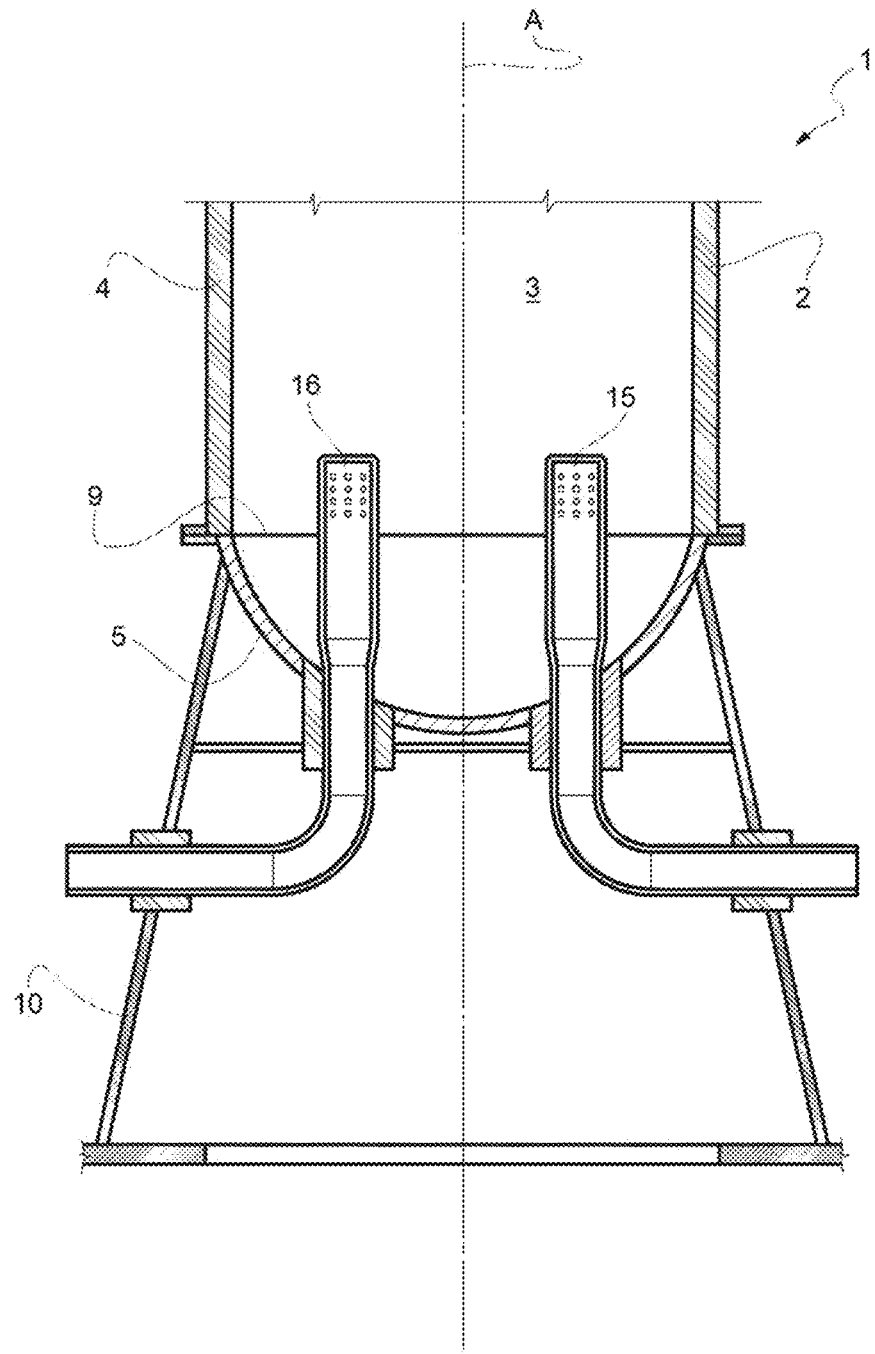
FIG. 1 is a schematic partial view, in longitudinal section, of the lower part of a urea synthesis reactor of one known configuration.
Figure 2:
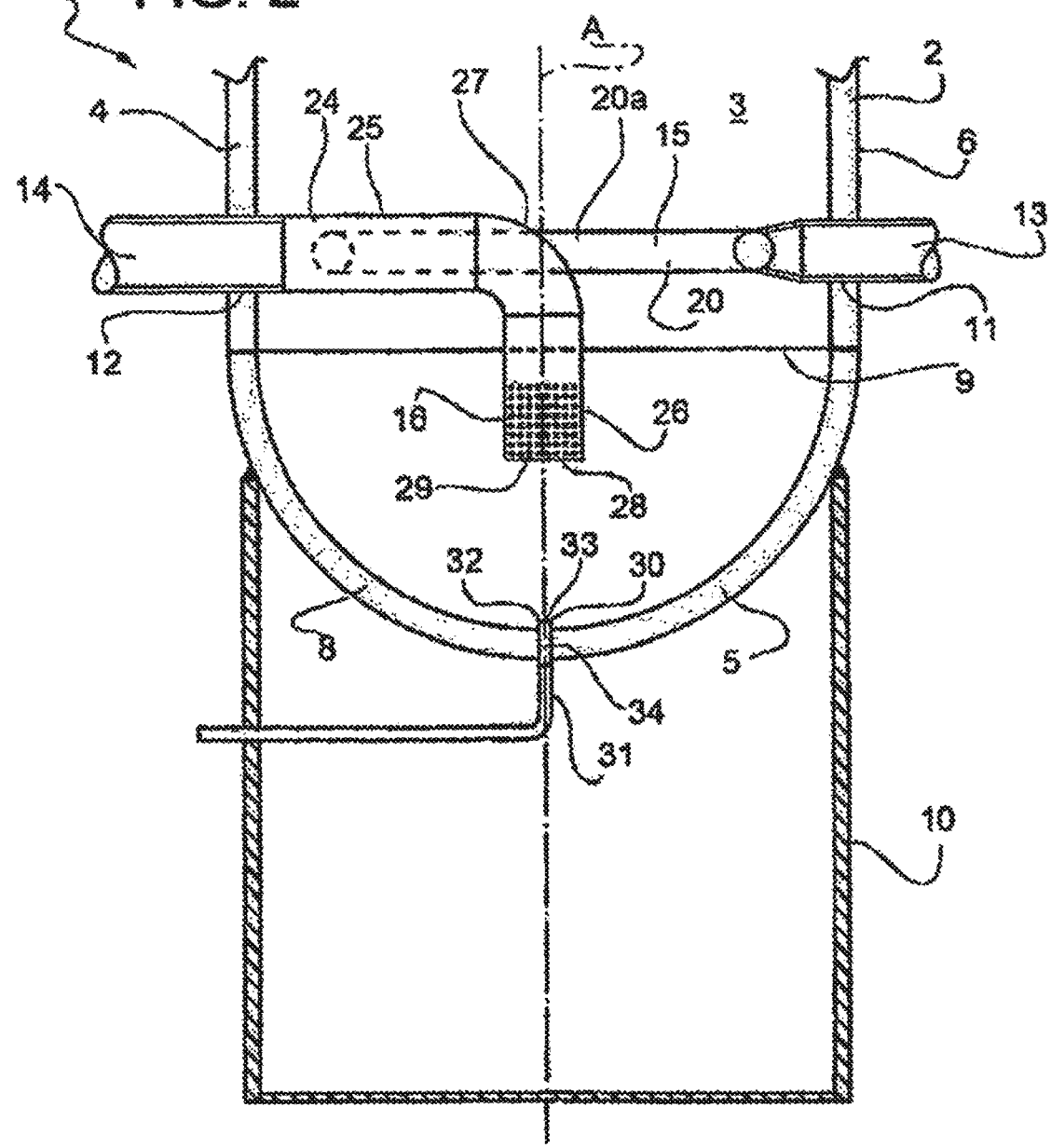
FIG. 2 is a schematic side elevation view, with parts in longitudinal section, of a urea synthesis reactor in accordance with the disclosure.

The casing 2 is substantially cylindrical and is closed at respective opposite axial ends by two end caps with, for example, a substantially hemispherical shape. FIG. 2 only shows the lower part of the reactor 1 and therefore only the end cap placed on the bottom end of the reactor 1, while the end cap placed on the top end and forming the head of the reactor is not visible.

With regard to the present disclosure, the casing 2 has an essentially cylindrical main portion 4 and a dome-shaped bottom portion 5 (in particular, substantially hemispherical) defining the bottom cap of the reactor 1.

The main portion 4 is delimited by a cylindrical side wall 6 about axis A.

The bottom portion 5 has a dome-shaped wall 8 and is joined to the main portion 4 along an essentially circular peripheral edge 9 (welding line), which lies on a plane substantially orthogonal to axis A.

The casing 2 is supported by a support frame 10, mechanically connected, in particular, to the bottom portion 5.

Figure 3:
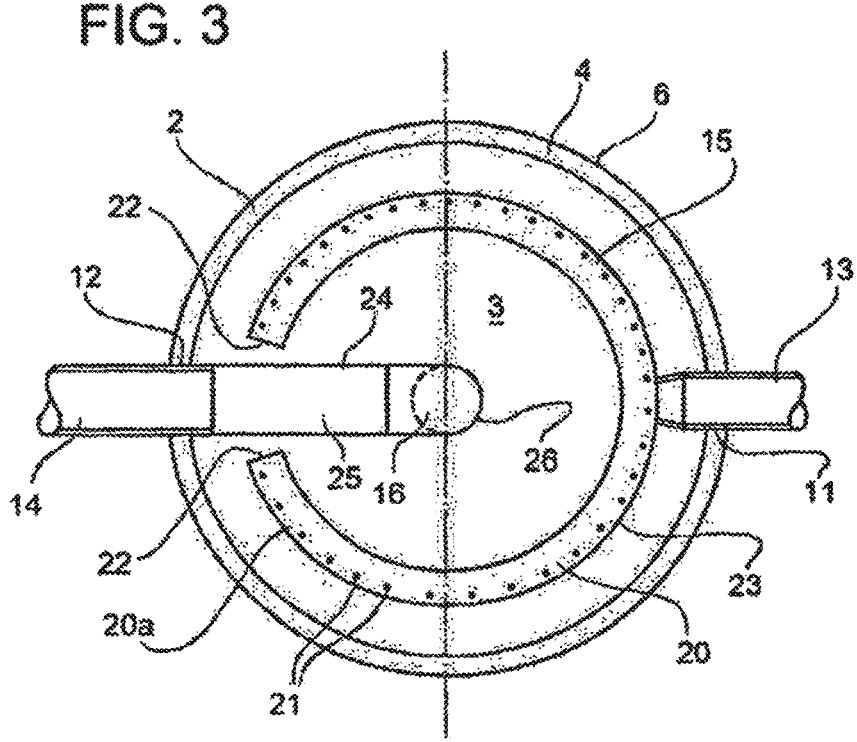
FIG. 3 is a schematic cross-sectional view of the reactor in FIG. 2.

Also referring to FIG. 3, the main portion 4 has a pair of lateral through openings 11 and 12 made in the side wall 6 above the edge 9 (i.e., above the joint line between the (cylindrical) main portion 4 and the (dome-shaped) bottom portion 5 of the casing 2).

In certain embodiments, the openings 11 and 12 are placed on opposite sides of a vertical middle-plane passing through the axis A of the reactor 1; in particular, the openings 11 and 12 are diametrically opposed.

In the non-limiting example in FIGS. 2 and 3, the openings 11, 12 are substantially aligned with one another, being placed more or less at the same distance (measured from the center of the openings 11, 12) from the edge 9.

Respective inlet tubes 13, 14 are inserted through the openings 11, 12 and are fluid-tightly connected, in a known manner, to the openings 11, 12, to feed the reagents of the urea synthesis reaction to the reactor 1: in particular, inlet tube 13 feeds a light phase (essentially gaseous) containing carbon dioxide, while inlet tube 14 feeds a heavy phase (essentially liquid) containing ammonia and generally also ammonium carbamate, to the reactor 1.

In the non-limiting example in FIGS. 2 and 3, the inlet tubes 13, 14 are parallel and substantially aligned with each other.

The inlet tubes 13, 14 are connected to respective reagent distributors 15, 16 inside the casing 2.

Distributor 15 (light phase distributor) comprises one or more tubular elements 20, connected to each other and/or to inlet tube 13 and extending/distributed over the cross-section of the reactor 1 and about axis A, and provided with intake holes 21 spaced apart from one another, so as to distribute the light phase in a plurality of intake points distributed transversely in the reactor 1 and about axis A.

In particular, the tubular elements 20 of the distributor 15 comprise an annular element 20a that projects from inlet tube 13 and is arranged about axis A along the side wall 6 and is, in certain embodiments, radially spaced apart from the side wall 6.

Inlet tube 13 projects radially outwards from the annular element 20a and is substantially coplanar with the annular element 20a, namely the inlet tube 13 and the annular element 20a are located substantially at the same height along axis A (i.e., at the same distance from edge 9).

Here and elsewhere, when speaking of the height or distance of a tubular component, it is intended that this height or distance is measured with respect to a central longitudinal axis of the tubular component.

The annular element 20a can be closed (i.e., have the form of a complete ring) or, as shown in FIGS. 2 and 3, be broken (i.e., have the form of an open ring).

In the non-limitative example shown, the annular element 20a has, in particular, an essentially toroidal shape with a substantially circular cross-section; the annular element 20a has a substantially circular shape in plan, but does not form a complete closed ring, but a broken ring, extending with an angular magnitude of less than 360°.

The annular element 20a is interrupted in a position diametrically opposite to inlet tube 13, where annular element 20a has two facing ends 22 placed on opposite sides of the inlet tube 14.

In certain embodiments, the ends 22 are blind (closed) ends; the annular element 20a is provided with a plurality of transverse intake through holes 21, made in a lateral wall 23 of the annular element 20a along the annular element 20a and angularly spaced apart from one another along the annular element 20a and about axis A. In certain embodiments, the holes 21 are uniformly distributed along the annular element 20a, in particular being uniformly spaced apart from one another along the annular element 20a.

In general, the holes 21 can be arranged in any position on the lateral wall 23; the holes 21 can therefore face upwards and/or downwards and/or towards the side wall 6 of the casing 2.

The holes 21 can be organized in one or more rows along the annular element 20a and/or can be staggered with respect to one another.

Distributor 16 (heavy phase distributor) comprises an essentially L-shaped tubular body 24: the tubular body 24 comprises a first substantially horizontal tube section 25 (constituted by inlet tube 14 or by an extension thereof) that projects from opening 12 substantially perpendicular to the side wall 6; and a second tube section 26 that projects from tube section 25 and is bent downwards (i.e., towards the bottom portion 5 of the casing 2).

In the example shown in FIG. 2, tube section 26 is bent by 90° with respect to tube section 25 and is therefore substantially vertical; in addition, tube section 26 is arranged centrally in the casing 2, substantially along axis A.

An elbow connector 27 connects tube section 25 to tube section 26; tube section 26 has a free end 28 opposite to the elbow connector 27; in certain embodiments, end 28 is a blind end, being closed by transverse wall, which could also be provided with holes (not shown); tube section 26 has a plurality of lateral through holes 29, made in a lateral wall of tube section 26 close to end 28.

Advantageously, the end 28 with the lateral holes 29 is placed at least partially (or entirely) in the bottom portion 5 of the casing 2 below edge 9.

Possible mechanical support members (for example, anchor brackets fixed to the side wall 6 of the casing 2) that support the tubular elements 20 (in particular, the annular element 20a) and/or the tubular body 24 or, more in general, the various components of the distributors 15 and 16 (not shown for simplicity).

The reactor 1 optionally includes also a light phase additional inlet 30.

The inlet 30 is defined by an auxiliary inlet tube 31 provided with at least one outlet hole 32; for example, the outlet hole 32 is located at an open free end 33 of the inlet tube 31.

The inlet tube 31 is of relatively small size, in particular, having a passageway section (cross-section) smaller than the inlet tubes 13, 14 and, in particular, than the light phase inlet tube 13.

The inlet tube 31 is arranged to pass through an auxiliary opening 34 made in the dome-shaped wall 8 of the bottom portion 5.

In certain embodiments, the inlet 30 is located centrally on the bottom portion 5 and the inlet tube 31 is substantially vertical and extends along axis A. The inlet tube 31 is also aligned with tube section 26 of the tubular body 24 and the outlet hole 32 faces and is aligned along axis A with end 28 of tube section 26 of the tubular body 24 (i.e., of the heavy phase distributor 16).

In certain embodiments, end 33 of the inlet tube 31 and the outlet hole 32 are on the dome-shaped wall 8 of the bottom portion 5 or close thereto, so as to also act as a drainage outlet of the reactor 1 when the reactor 1 must be emptied.

In use, the reactor 1 operates to implement the process of the disclosure as follows.

The reactor 1 is fed with a stream of carbon dioxide, constituting the (essentially gaseous) light phase of the urea synthesis reaction, via inlet tube 13 and distributor 15, and with a solution of ammonia/ammonium carbamate, constituting the (essentially liquid) heavy phase of the reaction, via inlet tube 14 and distributor 16.

Distributor 15 distributes the light phase (carbon dioxide) substantially uniformly over the cross-section of the reactor 1, in a plurality of intake points (defined by holes 21) distributed transversely in the reactor 1 and about axis A.

With respect to the previously described traditional solution, the annular (toroidal) geometry of distributor 15 and the distribution of holes 21 ensure more uniform distribution of carbon dioxide across the section of the reactor 1. This distribution is further favoured by the uniform flow field of the ammonia/carbamate solution achieved with the downward facing heavy phase distributor 16.

The downward orientation of distributor 16 and its positioning at the center of the cross-section of the reactor 1 along the central axis A of the reactor 1 ensures substantially uniform distribution of the (ammonia/carbamate) heavy phase throughout the volume of the reactor 1: in this way, the flow field of the ammonia inside the reaction chamber 3 is more uniform and constant with respect to the previously described traditional solution (with offset and upward facing inlets).

The optional additional feeding of the light phase via the additional inlet 30 further improves the mixing of the two phases in the lower region of the reactor 1, where first contact between the reagents takes place.

Figure 4:
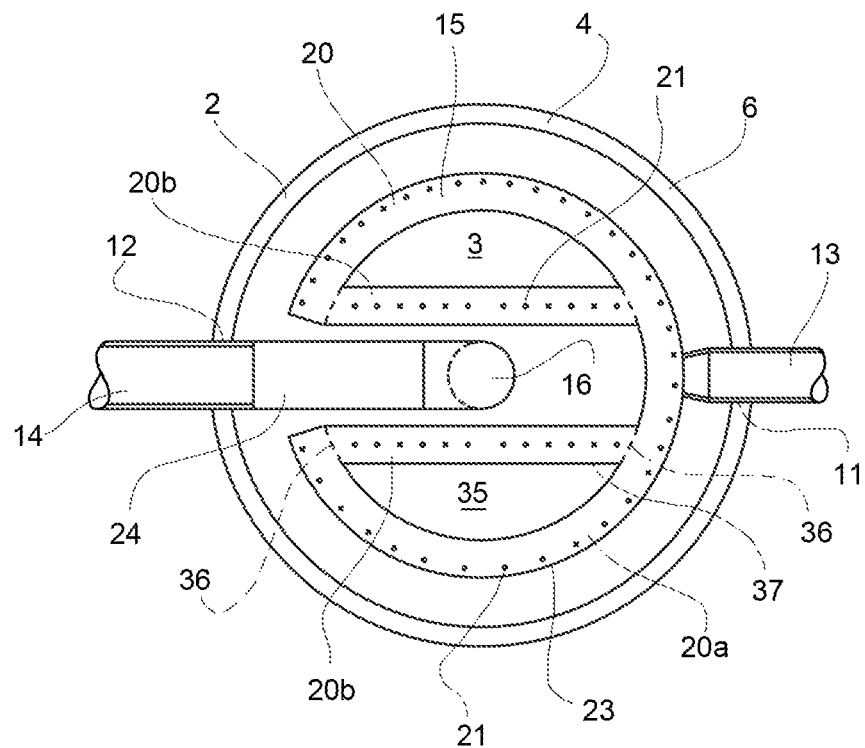
FIGS. 4 and 5 are schematic cross-sectional views of respective variants of the reactor in FIG. 2.
Figure 5:
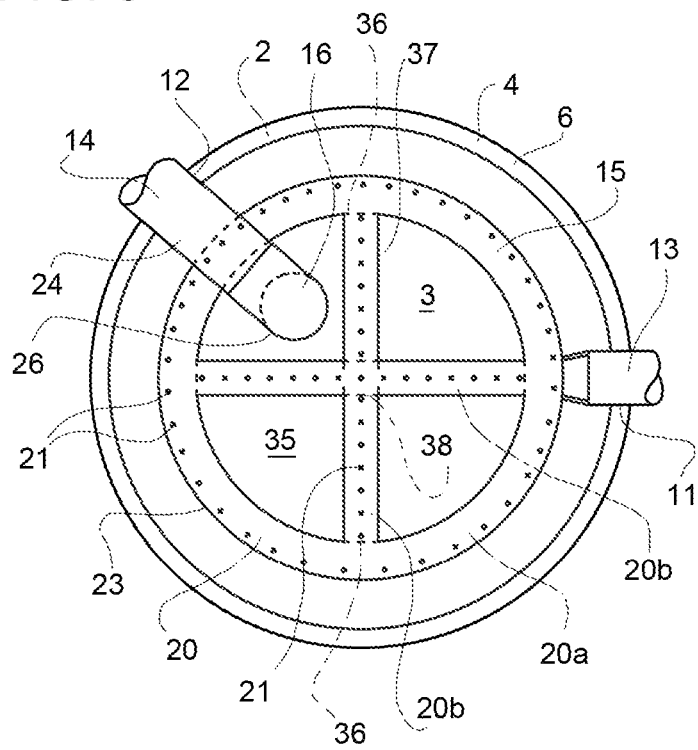

In the variants in FIGS. 4 and 5, in addition to the annular element 20a that projects from inlet tube 13 and is arranged along the side wall 6, the light phase distributor 15 comprises further tubular elements 20 constituted by respective arms 20b that project from the annular element 20a.

In certain embodiments, the arms 20b are substantially coplanar with the annular element 20a (i.e., they are substantially at the same height along the axis A as the annular element 20a).

The arms 20b, which are, for example (but not necessarily), substantially straight, extend in a space 35 radially delimited by the annular element 20a. In particular, each arm 20b connects a pair of radially inner junctions 36 of the annular element 20a facing each other on the lateral wall 23 of the annular element 20a.

Like the annular element 20a, each arm 20b is also provided with transverse intake through holes 21, formed in a lateral wall 37 of the arm 20b and spaced out (such as uniformly) along the arm 20b.

In the example in FIG. 4, the distributor 15 comprises a pair of straight arms 20b, parallel to each other and to inlet tube 13 and arranged on opposite sides of the inlet tube 14.

Each arm 20b extends between a junction 36 located close to an end 22 of the annular element 20a, and an opposite junction 36 located close to inlet tube 13 and laterally with respect to inlet tube 13.

In the example in FIG. 5, distributor 15 comprises a pair of straight arms 20b, perpendicular to each other and centrally joined in a cross. In particular, the arms 20b extend along respective diameters of the annular element 20a and connect respective diametrically opposed junctions 36 on the lateral wall 23 of the annular element 20a. In other words, distributor 15 comprises a plurality of radially internal arms 20b that project from the annular element 20a towards axis A and, in certain embodiments, join one another centrally in a central junction 38 arranged along axis A.

In this configuration, the heavy phase distributor 16 is, in certain embodiments, off-center with respect to the central axis A of the reactor 1 (i.e., instead on being placed centrally in the reactor 1 and along axis A, the heavy phase distributor is placed in an offset position with respect to axis A). In particular, tube section 26 provided with holes 29 is radially displaced with respect to axis A.

The openings 11, 12 and the inlet tubes 13, 14 can be at the same height along axis A, as previously described with reference to FIGS. 2 and 3, and in this case the annular element 20a is broken as previously described.

Alternatively, the openings 11, 12 are not aligned and neither are inlet tubes 13, 14 aligned. In particular, opening 11 and therefore inlet tube 13 are placed at a different height with respect to opening 12 and inlet tube 14, for example, at a lower height (i.e., at a smaller distance from edge 9): in this case, inlet tube 14 is placed above the annular element 20a and the annular element 20a can be shaped like a closed, complete ring.

Figure 6:
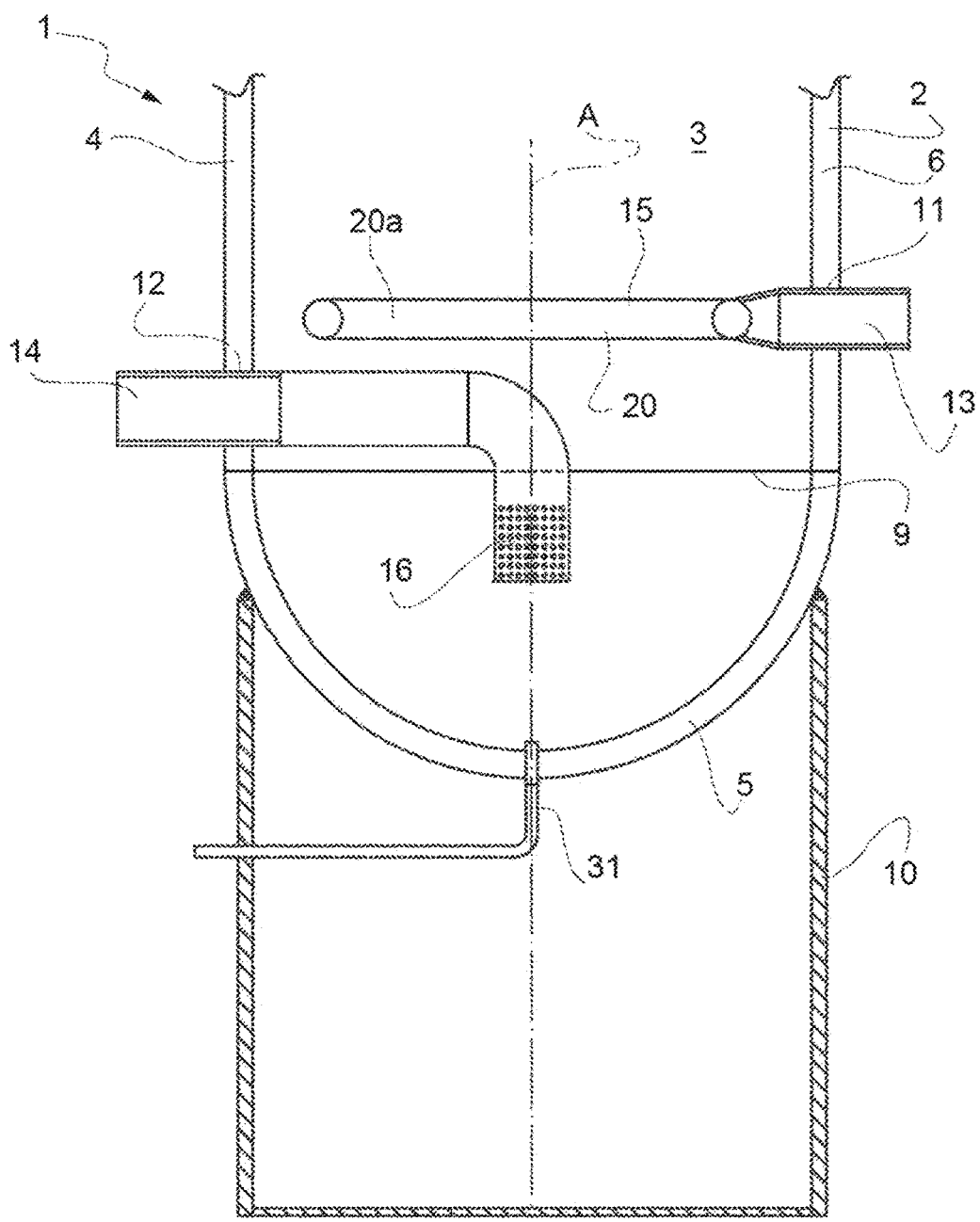
FIG. 6 is a schematic side elevation view, with parts in longitudinal section, of a further embodiment of the urea synthesis reactor of the disclosure.
Figure 7:
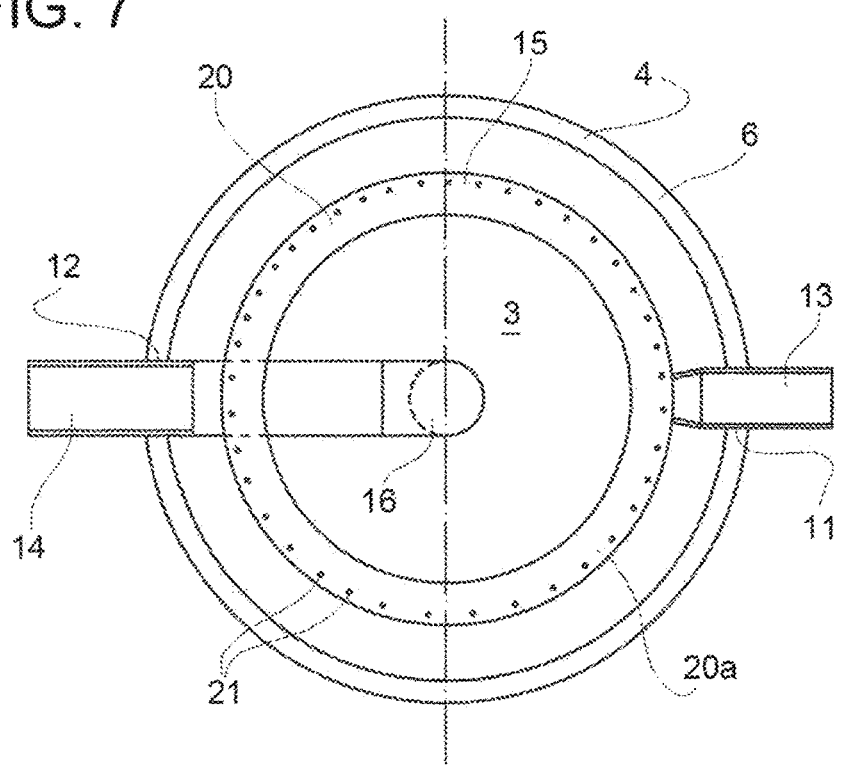
FIG. 7 is a schematic cross-sectional view of the reactor in FIG. 6.

In the embodiment in FIGS. 6 and 7, in which the same or similar details to those already described are indicated with the same reference numerals, the reactor 1 is also equipped with a pair of diametrically opposed inlet tubes 13, 14, inserted through respective diametrically opposed lateral through openings 11, 12 made in the side wall 6 of the casing 2 above edge 9, and connected inside the casing 2 to respective reagent distributors 15, 16.

In this case, the openings 1, 12 are not aligned but are axially staggered along axis A, being placed at different heights along axis A (i.e., at different distances measured from the center of the openings 11, 12) from edge 9. In particular, opening 11 is placed higher than opening 12.

Instead of being aligned, the respective inlet tubes 13, 14, always substantially parallel to each other, are also staggered along axis A, being arranged at different heights along axis A (i.e., at different distances from edge 9). In particular, the heavy phase inlet tube 14 is located below (closer to edge 9) the light phase inlet tube 13.

The distributors 15, 16 preserve the previously described general configuration. As the inlet tubes 13, 14 are axially staggered, the annular element 20a of the light phase distributor 15 can be shaped as a complete ring closed about axis A.

Figure 8:
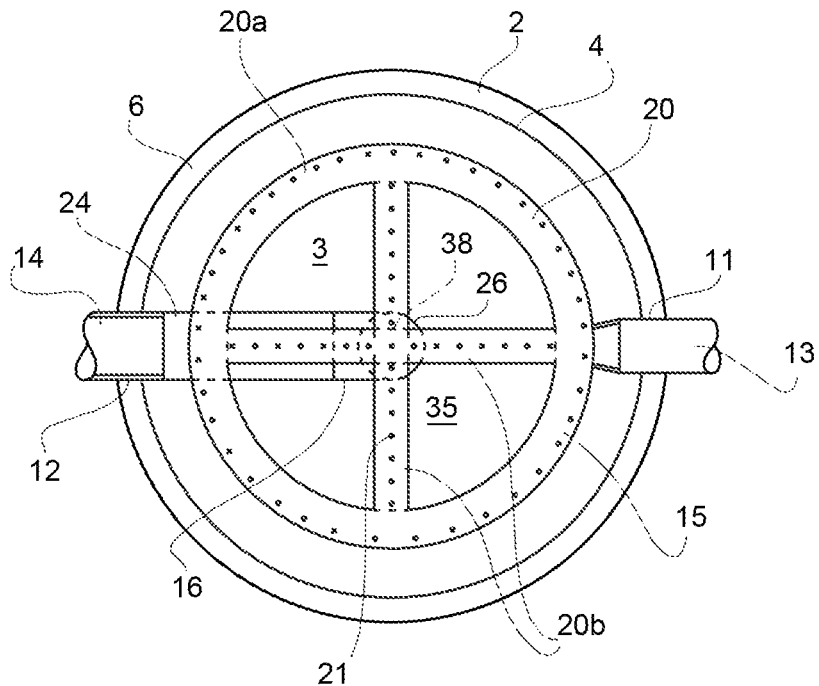
FIGS. 8 and 9 are schematic cross-sectional views of respective variants of the reactor in FIG. 6.

In the variant in FIG. 8, in addition to the annular element 20a that projects from the inlet tube 13 and is located along the side wall 6, the light phase distributor 15 comprises a pair of straight arms 20b perpendicular to each other and centrally joined in a cross (i.e., a plurality of radially internal arms 20b that project from the annular element 20a towards axis A and centrally join in a central junction 38 arranged along axis A).

Similarly to that described with reference to FIG. 5, the arms 20b are substantially coplanar with the annular element 20a. However, unlike the example in FIG. 5, in this configuration, the heavy phase distributor 16 (precisely, tube section 26 of the tubular body 24 with holes 29) is arranged centrally in the reactor 1 and along axis A, below the central junction 38 that joins the arms 20b.

Figure 9:
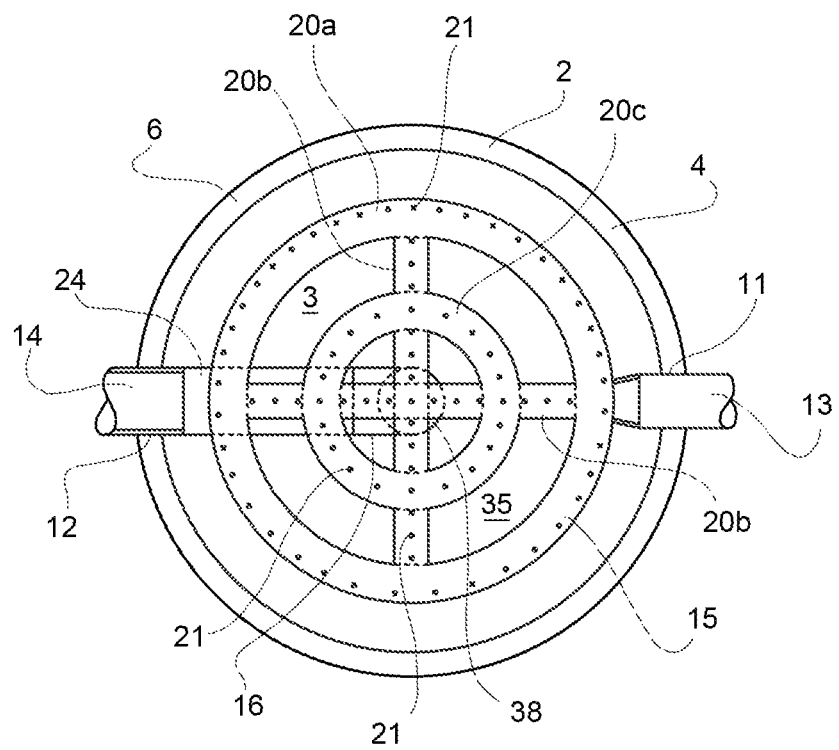

In the variant in FIG. 9, in addition to the annular element 20a, the light phase distributor 15 comprises one or more further annular elements 20c, concentric with the annular element 20a and placed radially inside the annular element 20a in space 35, and a plurality of radially internal arms 20b.

The annular elements 20c are also provided with intake holes 21, like the arms 20b.

The arms 20b, which are, for example, substantially straight, project from the annular element 20a towards axis A and connect the annular elements 20a, 20c and, in certain embodiments, join together centrally in a central junction 38 arranged along axis A.

It is understood that the solutions illustrated in the foregoing embodiments of the disclosure can be combined together in various ways.

Finally, it is understood that further modifications and variants can be applied to the reactor and to the urea synthesis process described and illustrated herein without departing from the scope of the appended claims. Accordingly, various changes and modifications to the presently disclosed embodiments will be apparent to those skilled in the art. Such changes and modifications can be made without departing from the spirit and scope of the present subject matter and without diminishing its intended advantages. It is therefore intended that such changes and modifications be covered by the appended claims.

The invention is claimed:

1. A urea synthesis process comprising:
   supplying a light phase containing carbon dioxide and a liquid heavy phase containing ammonia into a reactor extending along an axis and defining a reaction chamber wherein said light phase is supplied into the reactor through a first opening formed through a side wall of a main portion of a casing of the reactor, said first opening being above a peripheral edge joining the main portion of the casing with a dome-shaped bottom portion of the casing and said liquid heavy phase is supplied into the reactor through a second opening formed through the side wall of the main portion of the casing of the reactor, said second opening being above the peripheral edge joining the main portion of the casing with the dome-shaped bottom portion of the casing;
   distributing, at a plurality of intake points distributed transversely in the reactor about the axis, the light phase uniformly over a cross-section of the reactor about the axis; and
   centrally directing the liquid heavy phase downwards along the axis to radially distribute the liquid heavy phase in the reaction chamber.

2. The urea synthesis process of claim 1, wherein the intake points are set along at least one ring about the axis.

3. The urea synthesis process of claim 1, wherein at least two of the intake points are defined by respective intake holes angularly spaced apart from one another on at least one annular element positioned about the axis.

4. The urea synthesis process of claim 3, wherein at least two other intake points are defined by respective intake holes positioned on a plurality of arms projecting from the at least one annular element in a space radially delimited by the at least one annular element.

5. The urea synthesis process of claim 1, wherein supplying the light phase and the liquid heavy phase into the reaction chamber of the reactor further comprises supplying the light phase and the liquid heavy phase at different heights along the axis.

6. The urea synthesis process of claim 5, wherein the liquid heavy phase is additionally fed into the reaction chamber below the peripheral edge joining the dome-shaped bottom portion with the main portion of the reactor.

7. The urea synthesis process of claim 1, further comprising upwardly supplying an additional light phase stream in the reaction chamber, wherein the additional light phase stream is centrally circulated along the axis.

* * * * *